United States Patent [19]

Mazza

[11] Patent Number: 5,005,585
[45] Date of Patent: Apr. 9, 1991

[54] BIOPSY NEEDLE CONSTRUCTION

[75] Inventor: Joseph J. Mazza, Marshfield, Wis.

[73] Assignee: Marshfield Clinic, Marshfield, Wis.

[21] Appl. No.: 342,540

[22] Filed: Apr. 24, 1989

[51] Int. Cl.[5] .............................................. A61B 10/00
[52] U.S. Cl. ...................................................... 128/754
[58] Field of Search ............... 128/749, 751, 753, 754; 604/164, 170

[56] References Cited

U.S. PATENT DOCUMENTS

| | | | |
|---|---|---|---|
| 3,330,268 | 7/1967 | Goldsmith | 128/753 |
| 3,512,519 | 5/1970 | Hall . | |
| 4,099,518 | 7/1978 | Baylis | 128/2 B |
| 4,258,722 | 3/1981 | Sessions et al. | 128/753 |
| 4,262,676 | 4/1981 | Jamshidi | 128/753 |
| 4,314,565 | 2/1982 | Lee | 128/753 |
| 4,513,754 | 4/1985 | Lee | 128/753 |
| 4,543,966 | 10/1985 | Islam et al. | 128/754 |
| 4,643,196 | 2/1987 | Tanaka et al. | 128/753 |
| 4,649,918 | 3/1987 | Pegg et al. | 128/305 |
| 4,793,363 | 12/1988 | Ausherman et al. | 128/754 |
| 4,867,156 | 9/1989 | Stack et al. | 128/754 |

FOREIGN PATENT DOCUMENTS 553970  4/1977  U.S.S.R. ............................... 128/754

Primary Examiner—Max Hindenburg
Attorney, Agent, or Firm—Andrus, Sceales, Starke & Sawall

[57] ABSTRACT

A biopsy needle assembly comprising an outer tubular cannula having an angular distal end. The inner surface of the cannula adjacent the distal end is cylindrical and an end of the inner cylindrical surface opposite the distal end of the cannula is undercut to provide a sharp annular interior edge. A solid stylus is disposed within the cannula and has an angular distal end. The stylus is in sliding contact with the inner cylindrical surface of the cannula. When the needle assembly is inserted into engagement with the tissue to be removed a specimen is collected internally of the cannula and the sharp undercut interior edge secures the specimen within the cannula. After removal of the cannula from the tissue, a rod-like probe is inserted in the distal end of the cannula to push the specimen through the entire length of the cannula to remove the specimen intact.

10 Claims, 2 Drawing Sheets

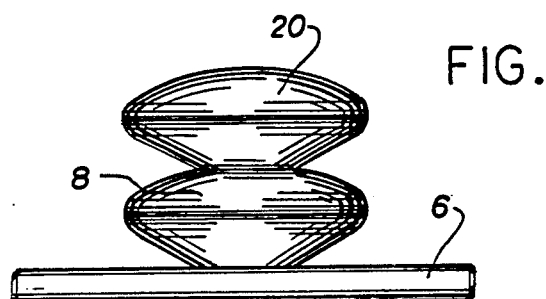
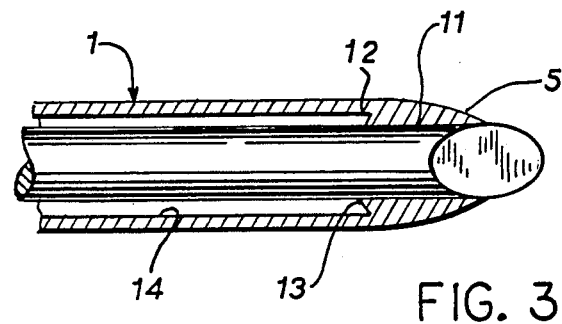
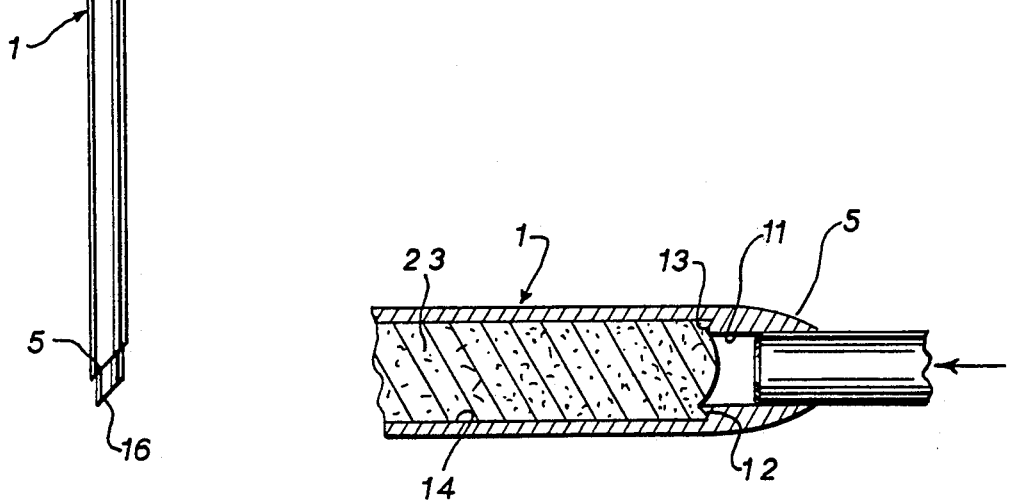
FIG. 2
FIG. 3
FIG. 4

BIOPSY NEEDLE CONSTRUCTION

BACKGROUND OF THE INVENTION

Bone marrow biopsy is a common minor surgical procedure that is an important diagnostic test in evaluating patients with primary hematological disorders and diseases that involve the bone and bone marrow. The procedure is a simple, brief and well tolerated operation, associated with extremely low morbidity and mortality. However, under certain circumstances a biopsy specimen may be difficult to obtain and may necessitate repeated attempts at biopsy in an effort to get adequate material for the study, thus lengthening the duration of the procedure and causing additional pain, discomfort and anxiety on the part of the patient.

In the past, the biopsy procedure has been carried out using a hollow needle of varying internal diameter with a tapered distal end and diagonal cutting edge. A rod-like stylus is inserted within the hollow needle and the assembly is then inserted into the patient's body until the tissue to be removed is engaged. When the distal end of the needle has reached the tissue from which the specimen is to be removed, the stylus is removed from the needle and the needle is rotated and urged forwardly. This movement produces a cutting action of the tissue and allows the specimen to be collected interiorly of the needle.

Although biopsy needles of this construction have met with success, failure to obtain an adequate core biopsy specimen frequently occurs. Not infrequently, the biopsy specimen will be left behind, either in the bone itself, or in the soft tissue outside the bone when the needle is withdrawn from the biopsy site, thus necessitating the need for another attempt or pass at obtaining a core biopsy.

SUMMARY OF THE INVENTION

The invention is directed to an improved biopsy needle assembly designed to securely retain core biopsy specimens and thus minimize the need for further passes at obtaining a core biopsy.

In accordance with the invention, the biopsy needle assembly comprises an outer tubular cannula and the distal end of the cannula is disposed diagonally with respect to its longitudinal axis. The inner surface of the cannula adjacent the distal end is cylindrical in shape and the end of the inner surface, opposite the distal end of the cannula, is undercut to provide a sharp annular interior edge, which is spaced axially from the distal end of the cannula. The remaining portion of the inner surface of the cannula, extending from the sharp undercut edge to the proximate end of the cannula, is of uniform internal diameter.

A solid rod-like stylus is adapted to be slidably received within the cannula, and a locking mechanism is provided to lock the stylus in proper orientation with respect to the cannula. The outer surface of the stylus is in sliding contact with the inner cylindrical surface that extends from the sharp annular edge to the distal end of the cannula and is spaced radially inward from the remaining portion.

In operation, the needle assembly, including the cannula and the stylus, is inserted into the patient's body until the tissue from which the specimen is to be removed is engaged with the distal end tip of the assembly. The stylus is then removed from the cannula and the cannula is rotated about its longitudinal axis while being urged forwardly. This movement provides a cutting action of the tissue and allows a specimen to be collected interiorly of the cannula. The cannula is then withdrawn from the patient's body and the sharp annular interior edge acts to hold the biopsy specimen against the lumen of the cannula while the cannula is withdrawn.

The specimen is then removed from the lumen of the cannula by inserting a solid metal rod or clearing probe into the distal end of the cannula and pushing gently through the entire length of the cannula, thus removing the biopsy specimen intact.

The biopsy needle assembly of the invention allows an operator to obtain a core biopsy specimen with a single pass while minimizing distortion and maintaining the configuration integrity of the biopsy specimen.

Because of the importance of size and quality of the biopsy specimens in many disorders, the varying gauge and length of the needle assembly enables an operator to obtain multiple large core biopsy specimens with minimal manipulation of the cannula and trauma to the patient.

Other objects and advantages will appear in the course of the following description.

DESCRIPTION OF THE DRAWINGS

The drawings illustrate the best mode presently contemplated of carrying out the invention.

In the drawings:

FIG. 2 is a paln view of the cannula with the stylus inserted therein;

FIG. 3 is a fragmentary enlarged longitudinal section of the distal end of the cannula with the stylus disposed therein; and FIG. 4 is a fragmentary enlarged longitudinal section of the cannula showing the manner of removing the biopsy specimen.

DESCRIPTION OF THE ILLUSTRATED EMBODIMENT

Figure 1:
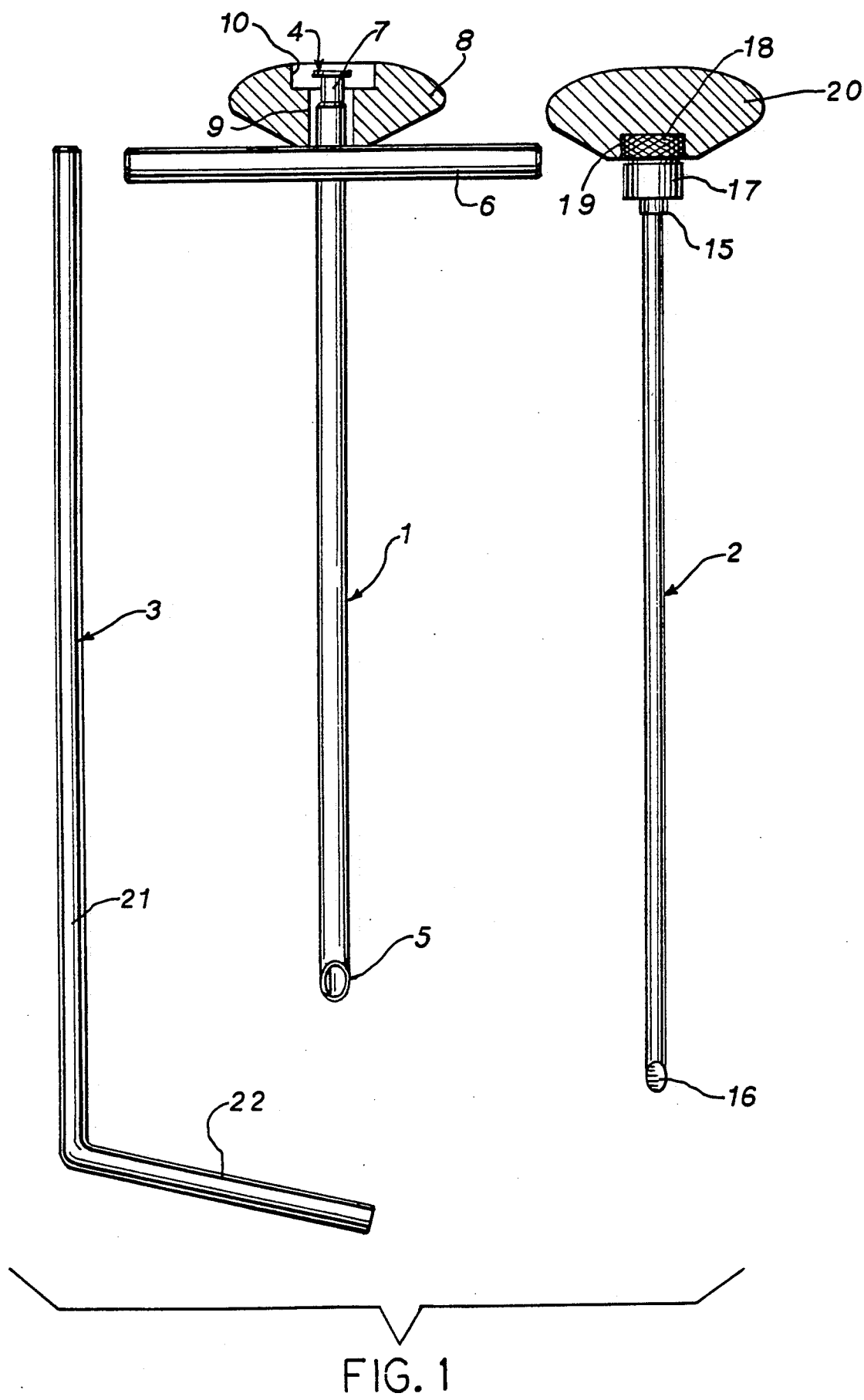
FIG. 1 is a plan view of the components of the biopsy needle assembly with parts broken away in section.

As illustrated in FIG. 1, the biopsy needle assembly is composed of three separate components, a hollow tubular cannula or needle 1, a solid intraluminar rod-like stylus 2, and a clearing rod or probe 3.

The components of the assembly are preferably formed of an alloy, such as stainless steel, which is corrosion resistant and non-toxic.

Cannula 1 has a proximate end 4 and a distal end 5 that is cut at an acute angle with respect to the longitudinal axis of the cannula and provides an annular cutting edge. A handle 6 is secured adjacent the proximate end 4 of the cannula, while a hub 7 is located at the proximate end. A knob or palm rest 8 is disposed around the proximate end 4 of the cannula and the knob 8 is provided with an axial passage 9 which is spaced from end 4 and the passage 9 terminates in an enlarged recess 10, which is spaced outwardly of hub 7.

As best illustrated in FIGS. 3 and 4, the distal end 5 of cannula 1 is formed with a cylindrical inner surface 11 and the end of surface 11 facing the proximate end 4 of the cannula is undercut, as indicated by 12, to provide a sharp annular interior edge 13.

As seen in FIGS. 2 and 3, the remaining portion of cannula 1, extending from edge 12 to end 4, as indicated by 14, and has a larger internal diameter than the cylindrical surface 11.

Stylus 2 has a proximate end 15 and a distal end 16, which is cut at an angle to the longitudinal axis of the stylus, with the angularity of distal end 16 being proximately the same as the angularity of distal end 5 of cannula 1.

Stylus 2 is in the form of a solid rod having a uniform external diamter throughout its length. A cup-shaped cover 17 is mounted on the proximate end 15 of the stylus, and when the stylus is inserted within cannula 1, cover 17 encloses hub 7 of the cannula. A knurled locking member 18 is mounted on proximate end 15 of stylus 2 and by rotating locking member 18, the hub cover will be locked with relation to hub 7 to prevent rotation of the stylus relative to cannula 1. As shown in FIG. 1, locking member 18 is mounted within a recess 19 formed in the inner surface of knob 20 of stylus 2.

When stylus 2 is inserted within cannula 1, distal end 16 of the stylus will contact and slide along the inner surface 11 of the cannula, while the remaining portion of the stylus will be spaced radially inward of the surface 14 of the cannular, as shown in FIG. 2.

After the stylus has been inserted within cannular 1, the stylus is rotated so that the diagonal distal end 16 is parallel to the distal end 5 of the cannula. The stylus 2 can then be locked against rotation relative to the cannula 1 by turning down of knob 20.

Clearing probe 3 includes a rod-like section 21, and an angular end 22 which extends laterally at an angle to section 21. Section 21 has an outer diameter the same as the outer diameter of stylus 2 and is adapted to be inserted into the distal end 5 of the cannula, after removal of the stylus and after cutting of the biopsy specimen, and serves to push the specimen to the proximate end 4 of the cannula where it is discharged, as will be hereinafter described.

In operation, the stylus 2 is initially inserted within cannula 1 and is rotated to orientate the diagonal distal end 16 of the stylus with the diagonal distal end 5 of the cannula. The stylus is then locked against rotation relative to the cannula by turning down of locking member 18.

The assembly, including the cannula 1 and stylus 2, is then inserted into a patient's body until the distal end of the cannula has reached the tissue from which the specimen is to be removed. Knob 20 and member 18 are then rotated to release the locking engagment between stylus 2 and cannula 1 and the stylus is then removed from the cannula. The cannula is then rotated about its longitudinal axis while it is urged forqardly by applying pressure to the palm rest 8. This movement produces a cutting action and allows a specimen 23 to be collected interiorly of the cannula, as seen in FIG. 4. As the specimen passes beyond the annular edge 13, it enters the large diameter section 14, thereby preventing crushing or compression of the selected specimen. When the cannula is withdrawn from the tissue, the annular edge 13 acts to hold the biopsy specimen inside the lumen of the cannula to prevent the specimen from adhering to the body.

The specimen 23 is then easily removed from the lumen of the cannula by inserting the section 21 of probe 3 into the distal end 5 of the cannula and pushing the section 21 gently through the entire length of the cannula, thus removing the biopsy specimen intact.

The biopsy needle assembly of the invention enables a biopsy specimen to be obtained with a single pass, and maintains the configuration and quality of the specimen without distortion.

While the biopsy needle assembly of the invention has particular application for obtaining bone biopsies for diagnostic purposes, it is contemplated that it can also be used for biopsy of the liver and thyroid, as well as other soft tissue organs.

Various modes of carrying out the invention are contemplated as being within the scope of the following claims particularly pointing out and distinctly claiming the subject matter which is regarded as the invention.

I claim:

1. A biopsy needle assembly, comprising an outer tubular cannula having a proximate end and a distal end, said distal end being disposed at an acute angle with respect to the longitudinal axis of said cannula, said cannula having an inner cylindrical surface disposed adjacent said distal end with said cylindrical surface having a uniform diameter throughout its length, an end of said cylindrical surface opposite said distal end being undercut to provide a sharp annular interior edge, the remaining portion of said cannula extending from said edge to said proximate end of said cannula having a larger internal diameter than the internal diameter of said cylindrical surface, and a solid stylus configured to be disposed within said cannula and having a proximate end and a distal end disposed at an acute angle to the longitudinal axis of said stylus, said stylus being in sliding contact with said cylindrical surface and spaced from said remaining portion of the cannula, the proximate end of said cannula being open, the distal end of said cannula after removal of said stylus acting to cut a specimen of tissue with the specimen being collected interiorly of said cannula and being removed through the open proximate end.

2. The assembly of claim 1, and including means for locking the stylus against rotation relative to said cannula.

3. The assembly of claim 2, and including a hub disposed adjacent the proximate end of said cannula, a cover disposed on the proximate end of said stylus and disposed around the hub when the stylus is inserted within said cannula, and locking means for locking said cover to said hub to thereby prevent rotation of said stylus relative to said cannula.

4. The assembly of claim 1 and including a handle disposed adjacent the proximate end of said cannula for rotating said cannula.

5. The assembly of claim 1, wherein the said remaining portion has a substantially uniform internal diameter throughout its length.

6. The assembly of claim 1, wherein said end of said cylindrical surface extends diagonally outward and in a direction toward said distal end to provide said undercut.

7. A biopsy needle assembly, comprising an outer tubular cannula having a proximate end and a distal end, said distal end being disposed at an acute angle with respect to the longitudinal axis of said cannula, said cannula having an inner cylindrical surface disposed adjacent said distal end, said cylindrical surface having a uniform diameter throughout its length, an end of said cylindrical surface opposite said distal end being undercut to provide a sharp annular interior edge, the remaining portion of said cannula extending from said edge to said proximate end of said cannula having a larger internal diameter than the internal diameter of said cylindrical surface, a solid stylus configured to be disposed within said cannula and having a proximate end and a distal end disposed as an acute angle to the longitudinal axis of said stylus, said stylus being in sliding contact with said cylindrical surface and spaced from said remaining portion of the cannula, a first knob connected to the proximate end of said cannula and having an outer surface, said proximate end of the cannula being open and the outer surface of said first knob being disposed outwardly of said proximate end.

8. The assembly of claim 7, and including a second knob connected to the proximate end of said stylus and disposed axially adjacent said first knob when said stylus is inserted in said cannula, and locking means interconnecting the knobs for locking the stylus against rotation relative to said cannula.

9. The assembly of claim 7, and including solid probe rod means having an external diameter sufficient to be disposed in sliding contact with said cylindrical surface, said probe means being inserted into the distal end of said cannula to push the specimen through the entire length of said cannula for discharge from said proximate end.

10. The assembly of claim 9, wherein said probe rod means includes a straight section disposed to be inserted within said cannula, and a handle section extending laterally from said straight section.

* * * * *